United States Patent
Onishi et al.

(10) Patent No.: US 6,927,408 B2
(45) Date of Patent: Aug. 9, 2005

(54) APPARATUS FOR AND METHOD OF INSPECTING SHEET BODY

(75) Inventors: Kazuo Onishi, Fujinomiya (JP); Hiroyuki Nishida, Fujinomiya (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 313 days.

(21) Appl. No.: 10/176,054

(22) Filed: Jun. 21, 2002

(65) Prior Publication Data

US 2003/0006549 A1 Jan. 9, 2003

(30) Foreign Application Priority Data

Jun. 28, 2001 (JP) ........................................ 2001-197407

(51) Int. Cl.[7] .............................................. G01N 21/88
(52) U.S. Cl. .............................. 250/559.45; 250/559.4; 250/559.42; 356/239.1; 356/430
(58) Field of Search ........................ 250/559.41–559.46, 250/559.4, 223 R, 223 B; 356/237.1, 237.2, 239.1, 239.2, 239.7, 239.8, 429, 430, 431

(56) References Cited

U.S. PATENT DOCUMENTS 5,452,079 A * 9/1995 Okugawa ............... 356/239.11
6,011,620 A * 1/2000 Sites et al. ............... 356/239.1

FOREIGN PATENT DOCUMENTS

JP         2-216437 A      8/1990

* cited by examiner

Primary Examiner—Kevin Pyo
(74) Attorney, Agent, or Firm—Sughrue Mion, PLLC

(57) ABSTRACT

When a film is rewound, light is applied from light-emitting units to the film, and light that has passed through the film is detected by light-detecting units to detect a plurality of inclined defects in the film based on a change in the intensity of the light transmitted through the film. Slits oriented in the direction of the inclined defects are disposed in front of the light-emitting units and the light-detecting units. Detected signals outputted from the light-detecting units are transmitted to a processing device and processed thereby. The processing device processes the signals by approximating a maximum value array of extremal values of the signals in respective reference lengths of the film, with two functions in zones, and identifying a boundary between the zones as a position where a defect disappears.

19 Claims, 13 Drawing Sheets

APPARATUS FOR AND METHOD OF INSPECTING SHEET BODY

BACKGROUND OF THE INVENTION

1. Field of the Invention

The present invention relates to an apparatus for and a method of inspecting a sheet body, and more particularly to an apparatus for and a method of inspecting a sheet body to detect a bend in the sheet body or a defect such as an irregularity of the thickness of a coated agent on the sheet body.

2. Description of the Related Art

A sheet body, such as a photographic film, for example, is manufactured according to a process including several steps as shown in FIG. 11 of the accompanying drawings.

The manufacturing process shown in FIG. 11 will be described below. In step S501, a sheet body serving as a film base is fabricated and wound around a core 500. Then, in step S502, the sheet body is unreeled from the core 500, coated with a photosensitive emulsion (silver halide or the like), and wound around another core 501.

Thereafter, in step S503, the sheet body coated with the photosensitive emulsion is severed to a suitable width and wound around another core 502. In step S504, the sheet body is cut off to product dimensions, inspected, packaged, and then shipped as photographic films.

As shown in FIG. 12 of the accompanying drawings, the sheet body as the film base has an end 400 that starts to be wound around the core 500. Since the end 400 provides a step due to its own thickness on the core 500, sheet coils wound around the end 400 are bent over the step. The bends of those sheet coils are progressively greater toward the core 500 and progressively smaller away from the core 500. The produced sheet body is cut to a given length and wound around the core 500 while the sheet body is being fed. Therefore, the end 400 of the sheet body is inclined to the axis of the core 500 depending on the speed at which the sheet body is fed when it is cut off and the speed at which the sheet body is cut by the cutter.

As a result, as shown in FIG. 13 of the accompanying drawings, the sheet body wound around the core 500 has a plurality of deformed areas 450 due to the bends in the respective sheet coils around the core 500 successively from the end 400, the deformed areas 450 being inclined at an angle φ to the axis of the core 500. The deformed areas 450 manifest themselves more greatly toward the core 500.

When the sheet body with the deformed areas 450 is coated with a photosensitive emulsion, the deformed areas 450 and other areas are not uniformly coated with the photosensitive emulsion. If the thickness of the applied photosensitive emulsion is not uniform, then images recorded on the photographic film tend to suffer density irregularities. Consequently, the deformed areas 450 need to be discarded as defective areas.

One conventional process of automatically detecting such defective areas of a sheet body is disclosed in Japanese Laid-Open Patent Publication No. 2-216437, for example. According to the disclosed conventional process, a parallel beam of light is applied to a light-transmissive sheet body, and a change in the amount of light that has passed through the light-transmissive sheet body is detected. If the light-transmissive sheet body has a defect such as a recess, the applied parallel beam of light is largely refracted and transmitted through the light-transmissive sheet body. Therefore, the amount of light that has passed through the light-transmissive sheet body is changed, and the defect is detected based on such a change in the amount of light transmitted through the light-transmissive sheet body.

The disclosed conventional process is effective to automatically detect relatively large defects of sheet bodies. However, it is difficult for the process to obtain a change in the amount of light which is caused by a small defect that can visually be judged by a skilled worker.

Therefore, it has been customary for a skilled worker to cut off a portion of the sheet body as a sample, develop an image on the sample, and determine whether there is a defect in the sample or not based on the developed negative, or to dispense with these steps and discard a relatively long sheet body portion including large safety margins.

However, the customary process of inspecting samples is time-consuming, and is further disadvantageous in that even skilled workers are likely to determine different sheet body lengths to be thrown away based on inspected results because the different skilled workers have different individual tendencies. The alternative process of discarding a relatively long sheet body portion including large safety margins is not preferable because normal areas are necessarily included in the discarded sheet body length.

SUMMARY OF THE INVENTION

It is a general object of the present invention to provide an apparatus for and a method of inspecting a sheet body to automatically and reliably detect a defective area in the sheet body.

A major object of the present invention is to provide an apparatus for and a method of inspecting a sheet body to automatically detect a small defect that can visually be judged by a skilled worker.

Another major object of the present invention is to provide an apparatus for and a method of inspecting a sheet body to reduce differences between sheet body lengths to be discarded and minimize the tendency to discard normal areas which would be included in discarded sheet body lengths.

Still another object of the present invention is to provide an apparatus for and a method of inspecting a sheet body to distinguish different sheet bodies from each other without the need for printing or embossing individual product numbers or the like on the sheet bodies.

According to the present invention, there is provided an apparatus for inspecting a light-transmissive sheet body to detect a stripe defect therein, comprising a light-emitting unit for applying light to the sheet body, a light-detecting unit for detecting light having passed through the sheet body, a slit member disposed in at least one of the light-emitting unit and the light-detecting unit, for shaping the light into a line of light through a slit defined in the slit member and guiding the line of light to the light-detecting unit, and a processor for processing signal data of the light detected by the light-detecting unit, the slit being oriented in the direction of the stripe defect, the processor comprising means for processing the signal data which is produced when the line of light is guided through the slit to the light-detecting unit to detect the stripe defect in the sheet body.

With the above arrangement, the defect in the sheet body can be detected accurately.

The sheet body may be fed relatively to the light-emitting unit and the light-detecting unit.

The sheet body may comprise a film coated with a photosensitive emulsion, and the stripe defect may comprise a defect formed by a step provided by an end of the film as wound around a core before the photosensitive emulsion is applied to the film.

Preferably, the slit has a width in the range from 0.1 mm to 1.0 mm.

The light emitted from the light-emitting unit and detected by the light-detecting unit may travel along an optical axis inclined to the normal to the sheet body by an angle ranging from 5° to 70°.

If the light has a wavelength ranging from 940 nm to 1310 nm and the sheet body comprises a photosensitive light, then the sheet body is not exposed to visible light.

The light-emitting unit and the light-detecting unit may be provided in a plurality of pairs spaced along the width of the sheet body.

The processor may comprise an extremal value calculator for determining an extremal value of the signal data for each reference length of the sheet body, and a defect disappearing position identifier for determining a first function established by a plurality of extremal values obtained from a range including the defect in the sheet, and a second function established by a plurality of extremal values obtained from a range not including the defect in the sheet, and identifying a position on the sheet body where the first function changes to the second function, as a defect disappearing position where the defect disappears.

The processor may further comprise a function corrector for correcting the second function determined by the defect disappearing position identifier with a predetermined coefficient, and the defect disappearing position identifier may comprise means for identifying a position on the sheet body where the first function changes to a corrected second function, as a corrected defect disappearing position where the defect disappears.

The light-detecting unit may comprise a condensing lens for converging the light having passed through the slit and a photoelectric transducer disposed at the focal point of the condensing lens.

A range representing ½ through ⅓ of a minimum interval of defects may be used as a zone length, and the reference length may be established as the sum of three successive zone lengths.

The light-emitting unit and the light-detecting unit may be provided in a plurality of pairs spaced along the width of the sheet body, and the defect disappearing position identifier may comprise means for identifying the defect disappearing position for each of the pairs of the light-emitting unit and the light-detecting unit and regarding a greater length from an edge to the defect disappearing position of adjacent defect disappearing positions as a length to be discarded of the sheet body.

According to the present invention, there is also provided a method of inspecting a light-transmissive sheet body to detect a stripe defect therein, comprising the steps of detecting light having passed through the sheet body with a light-detecting unit as a line of light oriented in the direction of the stripe defect, and processing signal data obtained from the line of light with a processor to detect the stripe defect in the sheet body.

The method may further comprise the steps of determining an extremal value of the signal data for each reference length of the sheet body, determining a first function established by a plurality of extremal values obtained from a range including the defect in the sheet, and a second function established by a plurality of extremal values obtained from a range not including the defect in the sheet, and identifying a position on the sheet body where the first function changes to the second function, as a defect disappearing position where the defect disappears.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

An apparatus for and a method of inspecting a sheet body according to the present invention, as applied to a sheet body inspecting apparatus for applying light to a light-transmissive film coated with a photosensitive emulsion and detecting a defect such as a bend in the light-transmissive film or an irregularity in the thickness of the applied photosensitive emulsion, will be described below with reference to FIGS. 1 through 10.

Figure 1:
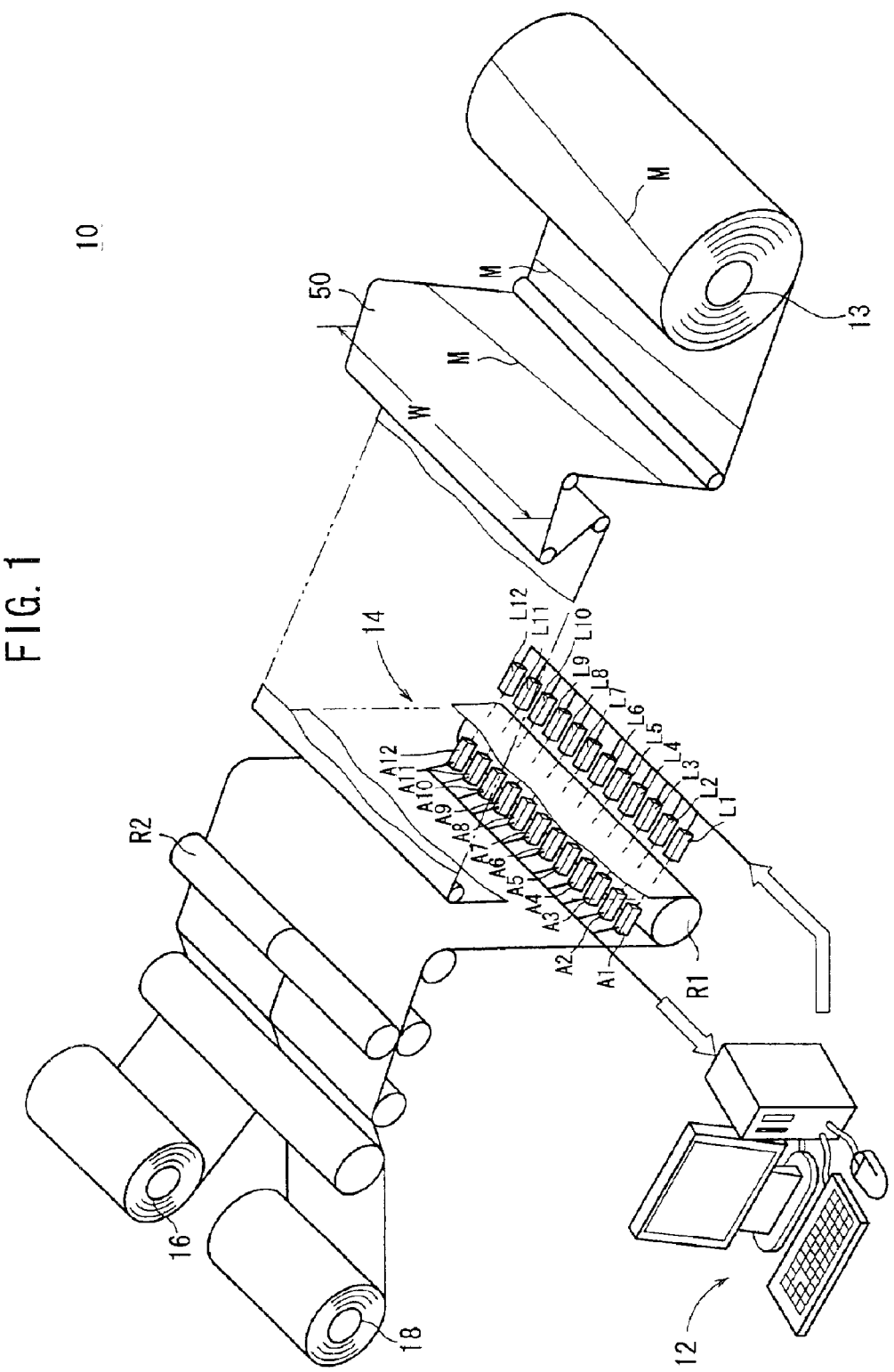
FIG. 1 is a perspective view of an apparatus for inspecting a sheet body according to the present invention.

As shown in FIG. 1, a sheet body inspecting apparatus 10 has a sensor system 14 for applying light to a light-transmissive film (sheet body) 50 and detecting light that has passed through the light-transmissive film 50, and a processing device (processor) 12 for processing a detected signal from the sensor system 14 to detect defects M present in the light-transmissive film 50.

Figure 11:
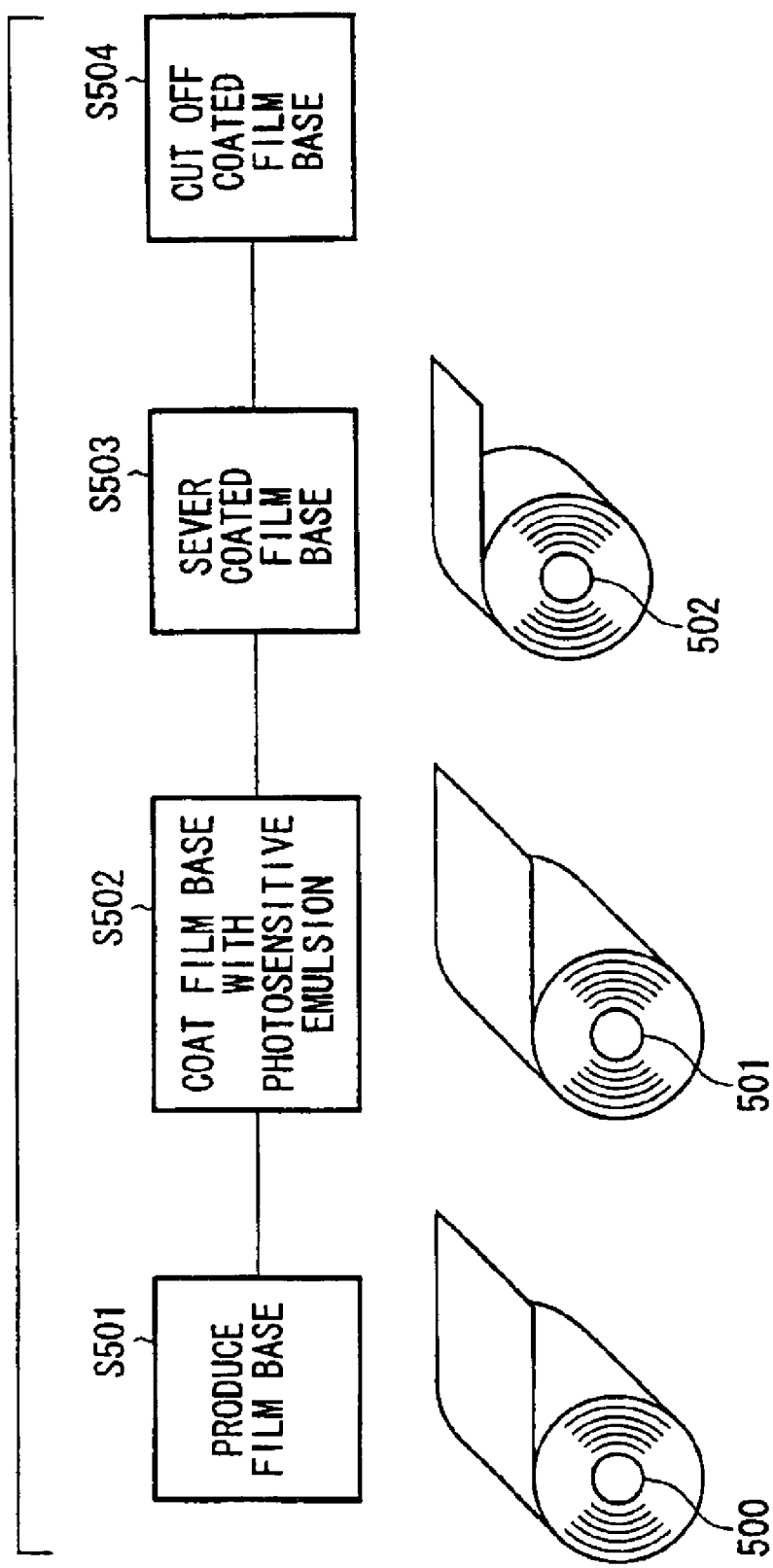
FIG. 11 is a perspective view illustrative of a conventional process of manufacturing a photographic film.
Figure 12:
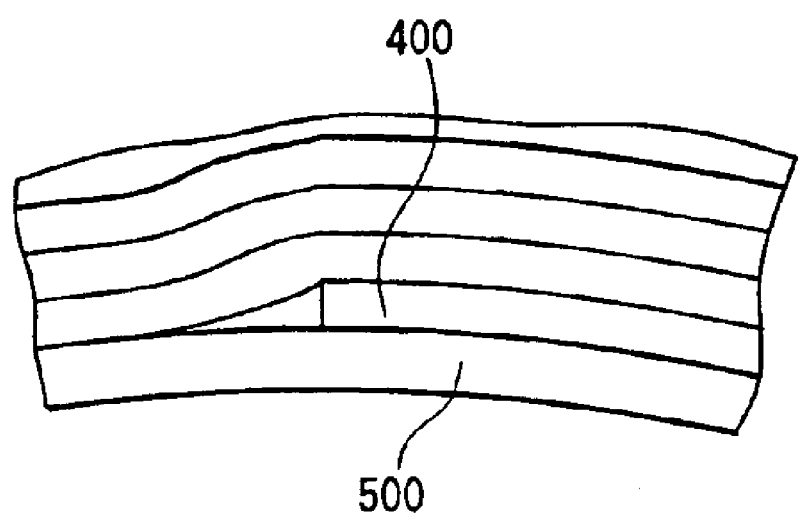
FIG. 12 is a view showing the manner in which defects are produced in a roll of photographic film.

The light-transmissive film 50 which is coated with a photosensitive emulsion is wound around a core 13. The light-transmissive film 50 is unreeled from the core 13 by a main feed roll R1 and cut by a slitting blade roll R2 into two sheet bodies, which are wound respectively around cores 16, 18. The film 50 as unreeled from the core 13 has a plurality of inclined defects M due to a step produced when the sheet body, prior to being coated with the photosensitive emulsion, is wound around the core 500 (see FIG. 11). The defects M are spaced at intervals each corresponding to the outer circumferential length of the core 500.

The sensor system 14 is disposed upstream of the main feed roll R1, and comprises 12 light-emitting units L1 through L12 spaced at equal intervals parallel to the width W of the film 50 and 12 light-detecting units A1 through A12 for detecting light emitted respectively from the light-emitting units L1 through L12 and transmitted through the film 50.

Figure 2:
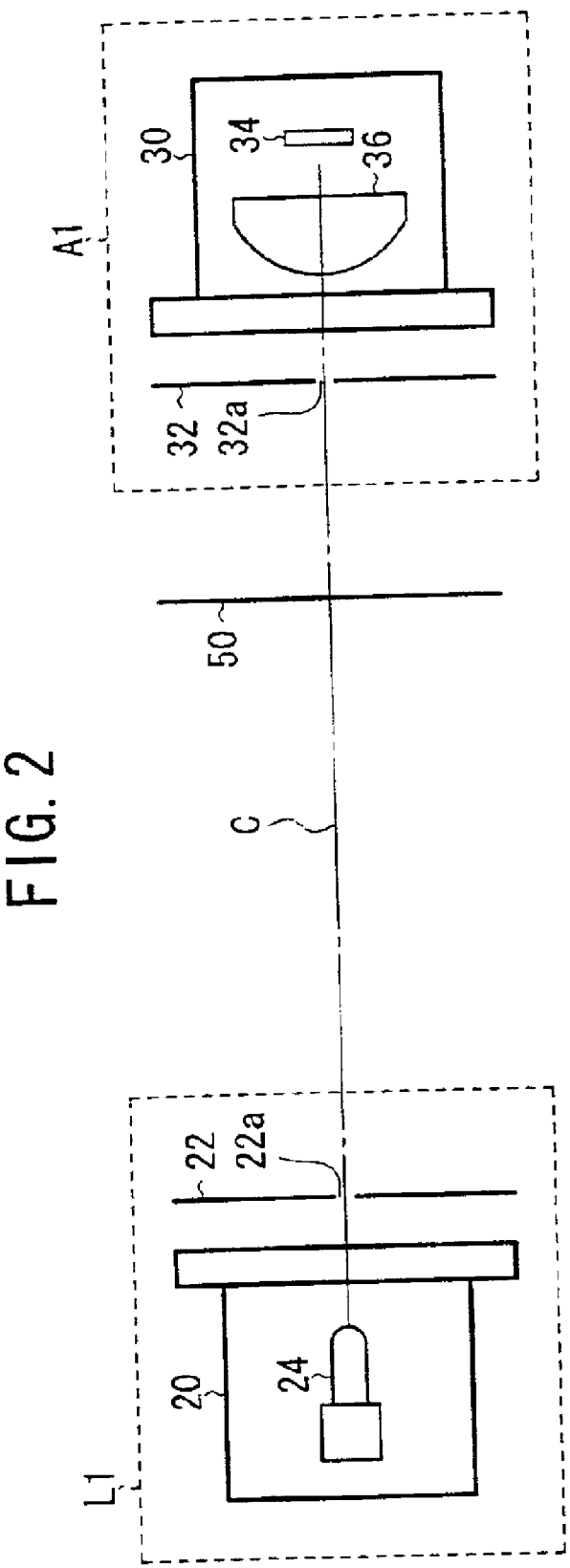
FIG. 2 is a schematic view of an arrangement of a light-emitting unit and a light-detecting unit incorporated in the apparatus shown in FIG. 1.

As shown in FIG. 2, the light-emitting unit L1 comprises a light-shielded housing 20, a light-emitting element 24 disposed in the housing 20 for emitting an infrared beam, and a slit plate 22 positioned in front of the housing 20 and disposed on the optical axis C of the light-emitting element 24. The other light-emitting units L2 through L12 are identical in structure to the light-emitting unit L1, and will not be described below.

The light-detecting unit A1 is positioned across the film 50 from the light-emitting unit L1, and has an optical axis aligned with the optical axis C of the light-emitting unit L1. The light-detecting unit A1 comprises a light-shielded housing 30, a condensing lens 36 disposed in the housing 30, a photoelectric transducer 34 disposed in the housing 30 and positioned on the optical axis C, and a slit plate 32 positioned in front of the housing 30. The condensing lens 36 is located such that the photoelectric transducer 34 has its photosensitive surface positioned at the focal point thereof. The other light-detecting units A2 through A12 are identical in structure to the light-detecting unit A1, and will not be described below.

The slit plates 22, 32 have respective slits 22a, 32a defined therein which extend in a direction perpendicularly to the optical axis C. The slits 22a, 32a have a width in the range from 0.1 to 1.0 mm.

Figure 3:
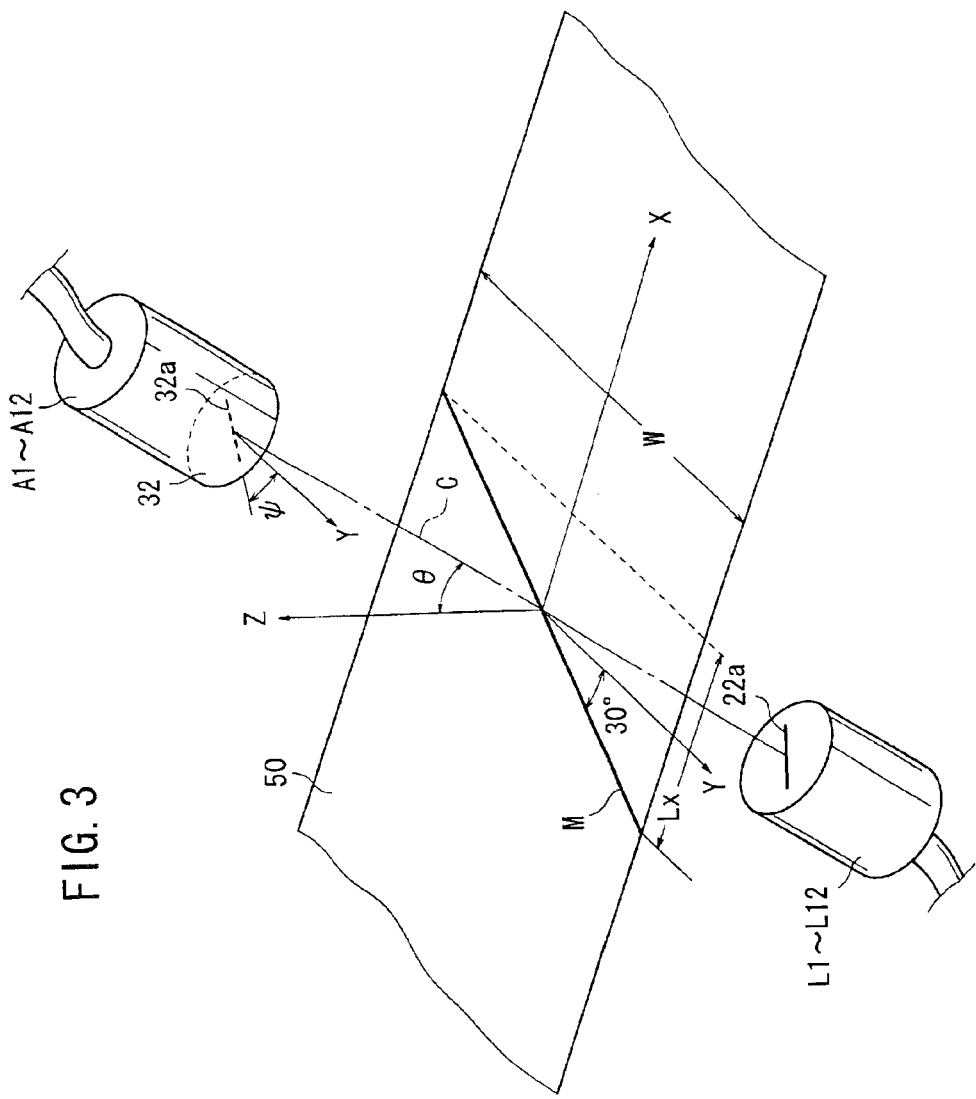
FIG. 3 is a perspective view showing the positional relationship between the light-detecting unit and a sheet body.

As shown in FIG. 3, the optical axis C of each of the light-detecting units A1 through A12 is inclined at an angle θ to the normal (Z-axis) to the film 50, toward the X-axis along which the film 50 is fed. The angle θ is preferably in the range from 5° to 70°.

The slit 32a defined in the slit plate 32 is oriented in alignment with the inclined defect M as viewed from each of the light-detecting units A1 through A12, and is inclined at an angle 104 to the Y-axis transversely across the film 50.

The angle 104 will be described below. If the defect M is inclined 30° to the Y-axis, then the length Lx of the defect M in the film 50 along the X-axis is expressed, using the width W of the film 50, by:

$$Lx = W \times \tan(30°) = W/\sqrt{3}$$

The length Lx is viewed as compressed by cos θ due to the angle θ from the position of each of the light-detecting units A1 through A12, and hence is represented by $(W/\sqrt{3}) \times \cos θ$. Therefore, the angle ψ by which the defect M is inclined, as viewed from each of the light-emitting units L1 through L12 and the light-detecting units A1 through A12, is expressed by:

$$\psi = \operatorname{Tan}^{-1}((W/\sqrt{3}) \times \cos θ / W)$$

$$= \operatorname{Tan}^{-1}(\cos θ / \sqrt{3}) \quad (1)$$

The angle ψ by which the slit 22a of each of the light-emitting units L1 through L12 is expressed in the same manner as described above.

Figure 4:
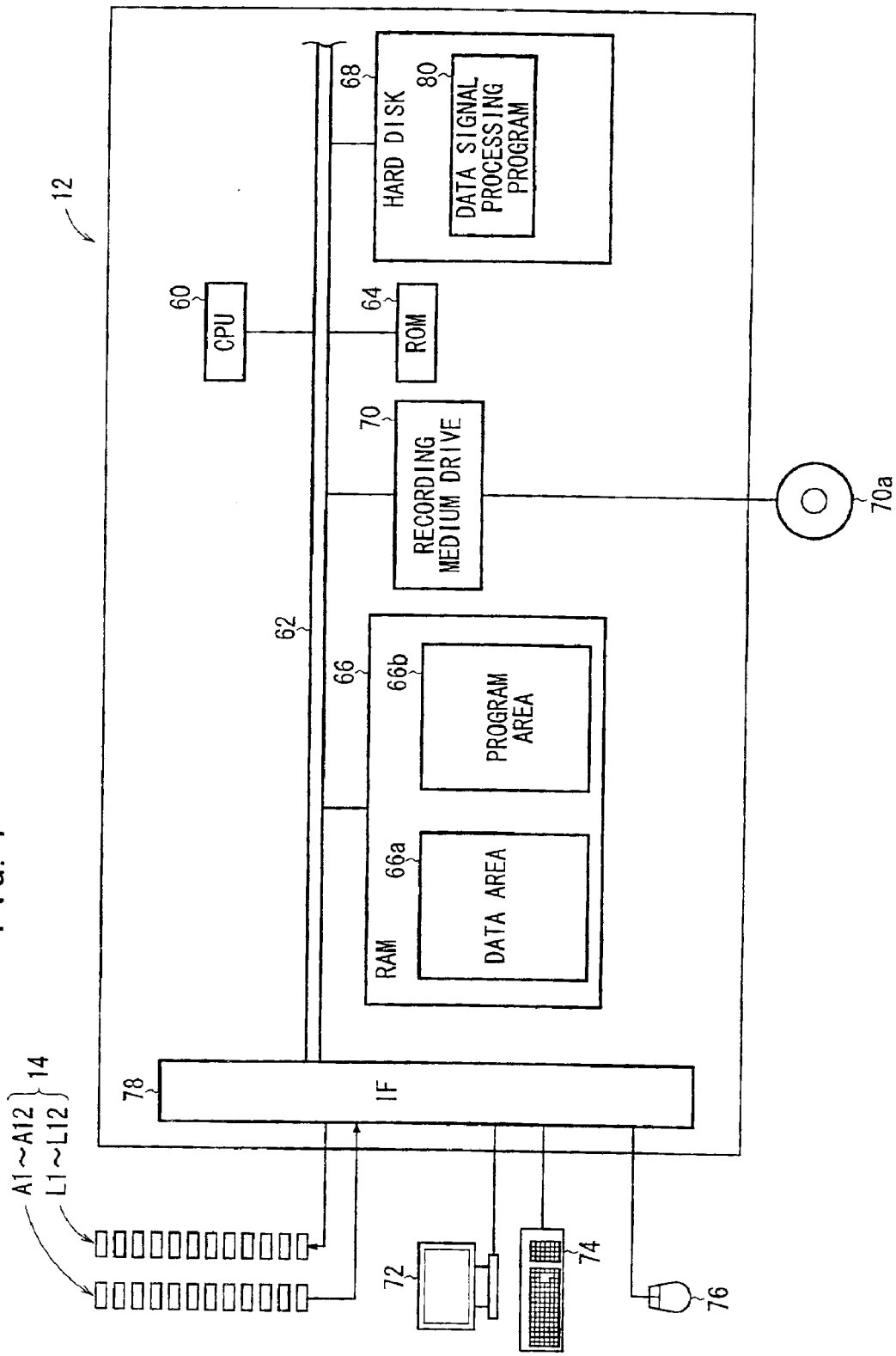
FIG. 4 is a block diagram of a processing device of the apparatus shown in FIG. 1.

As shown in FIG. 4, the processing device 12 comprises a CPU (Central Processing Unit) 60 for controlling the processing device 12 in its entirety through a bus 62, a ROM (Read Only Memory) 64 as a nonvolatile memory, a RAM (Random Access Memory) 66 as a memory, a hard disk 68 for storing programs and other data, a recording medium drive 70 for controlling an external recording medium 70a such as an optical disk, a magnetic disk, or the like, a display monitor 72 as a display unit, a keyboard 74 and a mouse 76 as an input device, and an interface (IF) 78 for controlling the transfer of signals between the display monitor 72, the keyboard 74, the mouse 76, and the sensor system 14.

The RAM 66 has a data area 66a for storing data read from the sensor system 14 and a program area 66b for loading programs from the hard disk 68.

The hard disk 68 stores a data signal processing program 80 for processing signal data received from the light-detecting units A1 through A12 and an OS (Operating System).

Operation of the sheet body inspecting apparatus 10 thus constructed will be described below with reference to FIGS. 5 through 10.

Figure 5:
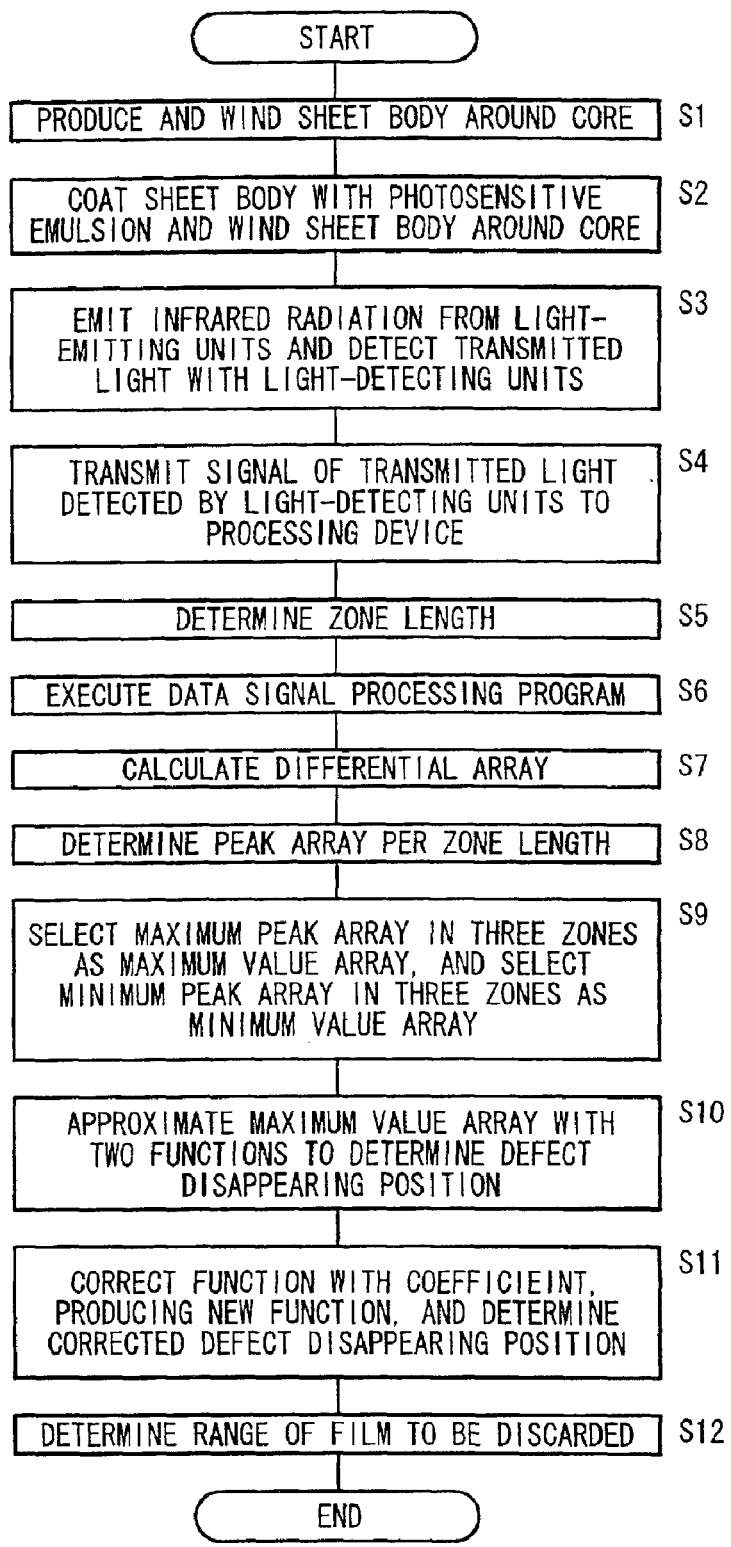
FIG. 5 is a flowchart of a method of inspecting a sheet body according to the present invention.
Figure 6:
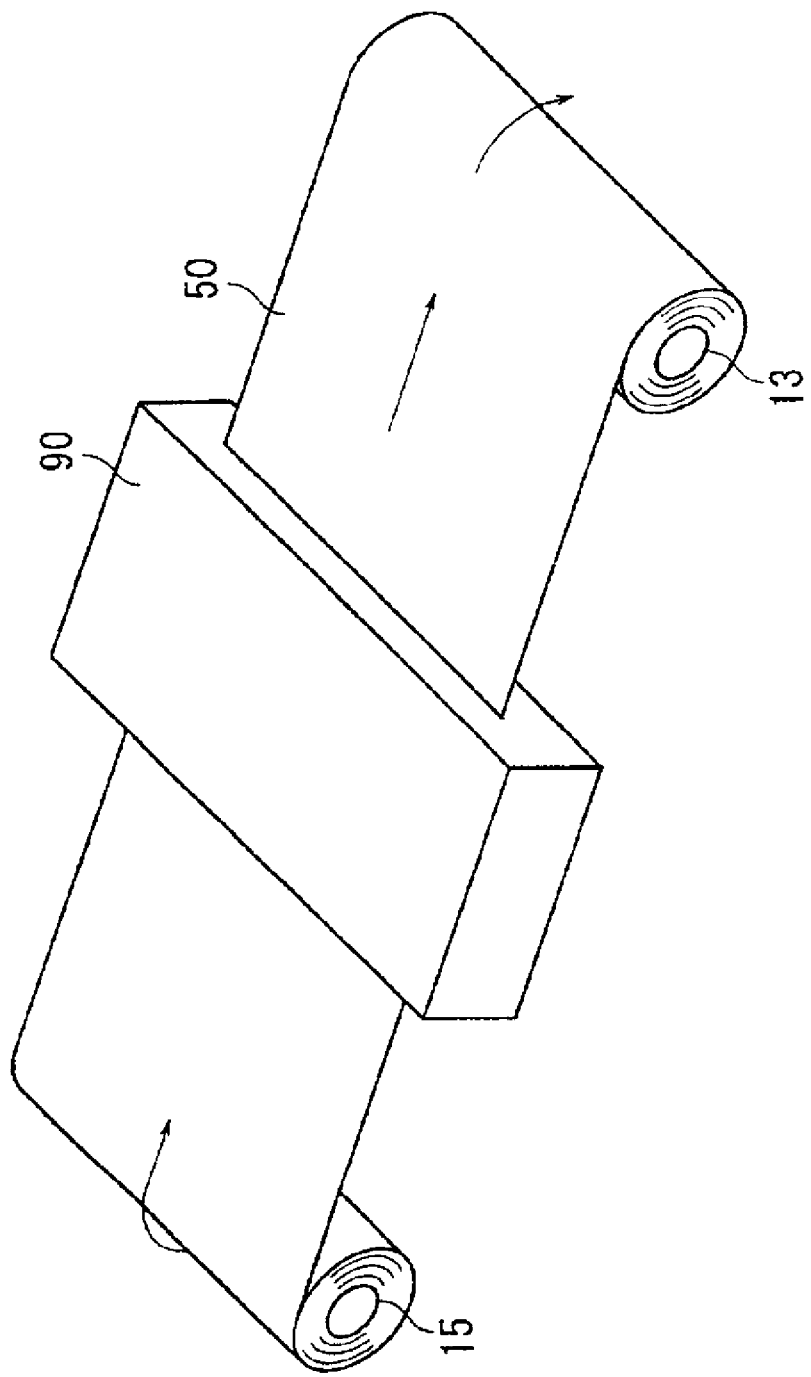
FIG. 6 is a perspective view illustrative of a step of coating a sheet body with a photosensitive emulsion.

In step S1 shown in FIG. 5, a sheet body is manufactured as a base of the film 50.

Figure 13:
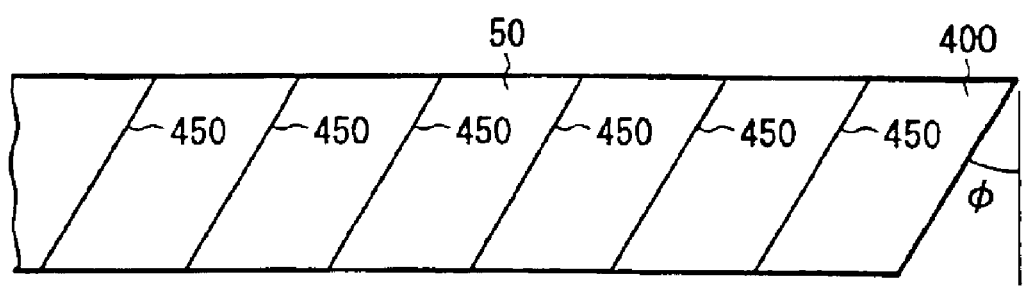
FIG. 13 is a view showing defects in the photographic film that are positioned successively from an end of the photographic film.

The shape of the end of the sheet body is determined depending on the speed at which the sheet body is fed when it is cut off and the speed at which a cutting blade moves to cut the sheet body in a direction perpendicular to the direction in which the sheet body is fed. As described above with reference to FIG. 13, the end of the sheet body is inclined at a certain angle to the Y-axis transversely across the sheet body.

The cut sheet body is wound around a core 15 having a diameter of 300 mm. At this time, each time one coil of the sheet body is wound around the core 15, a defect M is developed in the sheet body by the step that is produced by the cut end of the sheet body. The defect M is inclined at an angle that is equal to the angle at which the end of the sheet body is inclined to the Y-axis. The sheet body is deformed more largely by the defect M toward the core 15.

In step S2, the sheet body is unreeled from the core 15, and coated with a photosensitive emulsion by an emulsion applicator 90 (see FIG. 6), forming a film 50 which is wound around another core 13. At this time, the photosensitive emulsion is not uniformly applied to the area of the sheet body which includes the defect M. The defect M in the film 50 is positioned on the outer circumferential surface of the film 50 as it is wound around the core 13.

The outer circumferential surface of the film 50 as it is wound around the core 15 is free of deformations, and is uniformly coated with the photosensitive emulsion by the emulsion applicator 90. The film 50 which is wound around the core 13 after having been uniformly coated with the photosensitive emulsion is liable to be deformed by the step developed by the cut end on the core 13, but no irregularities are caused in the thickness of the applied photosensitive emulsion by the deformation.

The film 50 wound around the core 13 is delivered to another production line where the film 50 is cut into two sheet bodies. Specifically, as shown in FIG. 1, the film 50 is unreeled from the core 13 by the main feed roll R1 and cut by the slitting blade roll R2 into two sheet bodies, which are wound respectively around cores 16, 18.

In step S3, the light-emitting units L1 through L12 of the sensor system 14 emit light, and the light-detecting units A1 through A12 detect light that has passed through the film 50. The light-emitting element 24 emits an infrared beam whose wavelength is in the range from 940 nm to 1310 nm to prevent exposure of the photosensitive emulsion, i.e., silver halide.

The slits 22a, 32a inclined at the angle ψ determined according to the equation (1), which corresponds to the angle (30° in FIG. 3) at which the defect M is inclined, are disposed in front of the light-emitting units L1 through L12 and the light-detecting units A1 through A12.

A line of light produced by the slits 22a, 32a reaches the photoelectric transducers 34 of the light-detecting units A1 through A12. Since the line of light is inclined at an angle which is the same as the angle at which the defect M is inclined, when the defect M passes through the path of light, the transmittance of the film 50 is changed simultaneously along the line of light, and hence the amount of light detected by the photoelectric transducers 34 is changed greatly. Therefore, even if the transmittance of the film 50 is high, it is possible to detect, with high accuracy, whether the film 50 has a defect M or not.

Either one of the slits 22a, 32a for producing a line of light may be employed, and the other dispensed with.

In the present embodiment, the optical axis C is inclined at the angle θ in the range from 5° to 70° to the normal to the film 50. Therefore, the length of the path of light is increased, and the transmittance is reduced, making it possible to detect the defect M with higher accuracy.

Light emitted from the light-emitting elements 24 of the light-emitting units L1 through L12 is not focused onto the film 50, but focused onto the photoelectric transducers 34 by the condensing lenses 36 of the light-detecting units A1 through A12. Therefore, even if the film 50 is positionally displaced along the axis C while it is being fed, the defect M can be detected highly accurately without being affected by such a positional displacement of the film 50.

The light that has passed through the film 50 and has been detected by the light-detecting units A1 through A12 is sent as output signals from the light-detecting units A1 through A12 to the processing device 12. The processing device 12 measures the output signals in 12 channels from the light-detecting units A1 through A12 at each interval of 1 mm along the direction in which the film 50 is fed, and stores the measured data signals as digital values in the data area 66a in step S4.

Subsequent steps S5 through S12 represent a process for processing the stored data signals in the processing device 12.

In step S5, a zone length D for processing the data signals is determined. The zone length D is determined in order to process data signals including coating irregularities of the photosensitive emulsion due to the defect M and data signals including coating irregularities of the photosensitive emulsion irrespective of the defect M, separately from each other.

The zone length D is determined according to a condition 2D<K<3D where K represents the outer circumferential length (mm) of the core 15 on which the defect M is developed. The minimum interval between adjacent defects M is equal to the outer circumferential length K of the core 15, and becomes progressively greater as the sheet body is wound as successive coils around the core 15. If the interval between adjacent defects M does not change greatly from the minimum outer circumferential length K, then under the condition 2D<K<3D, when three adjacent zones are selected, a data signal including the defect M is present in one of the three zones, and a data signal not including the defect M is present in the other two zones. Specifically, since the outside diameter of the core 15 is 300 mm, the outer circumferential length K is K=300×π=about 942 mm, and hence the zone length D is determined under the condition 314<K<471. It is assumed in the following description that D=400 mm. The determined zone length D is supplied to and stored in the processing device 12.

In step S6, the CPU 60 loads a data signal processing program 80 into the program area 66b, and executes the data signal processing program 80 to perform a signal processing sequence described below.

In step S7, the CPU 60 and the data signal processing program 80 produce a signal sequence x(1) through x(max) of data signals read from the light-detecting unit A1. Since the processing device 12 measures the data signals at successive intervals of 1 mm in the direction in which the film 50 is fed, if the film 50 has a length of 200 m, then the maximum number of data signals is max=200000.

The CPU 60 and the data signal processing program 80 then calculate a differential array dx5(i) through dx40(i) of 36 differential data from the signal sequence x(1) through x (max), where dx5(i)=x(i+5)−x(i), dx6(i)=x(i+6)−x(i), . . . , dx40(i)=x(i+40)−x(i), i=1 through max.

The differential array dx5(i) through dx40(i) represent differential data between the data signals corresponding to a distance ranging from 5 to 40 mm in the direction in which the film 50 is fed, on the assumption that coating irregularities of the photosensitive emulsion occur in a range from 5 mm to 40 mm. A defect M can reliably be detected from the maximum value of the differential data. The range for coating irregularities of the photosensitive emulsion and the corresponding differential array can be changed as desired.

Figure 7:
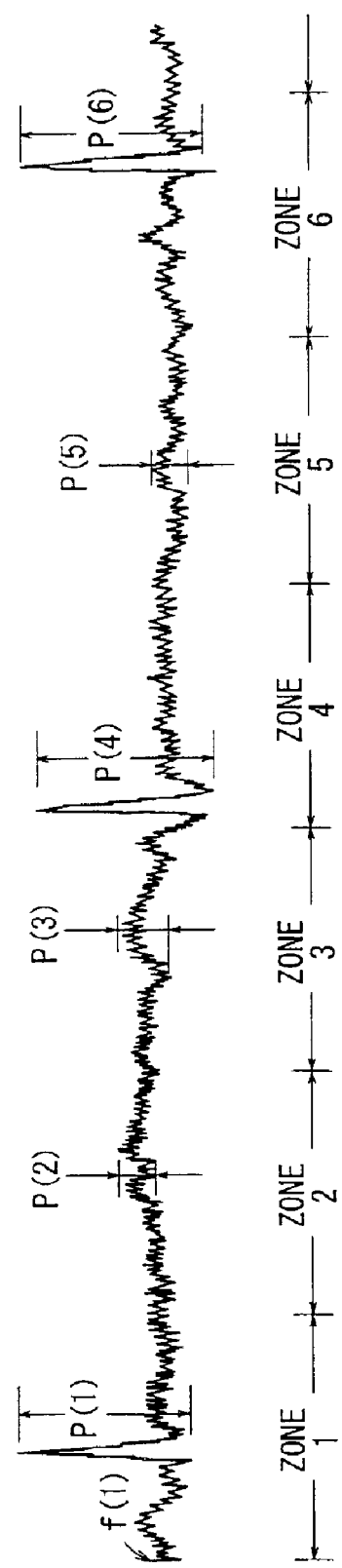
FIG. 7 is a diagram showing peak values determined in respective zones of the waveform of an output signal from the light-detecting unit.

In step S8, the maximum value of the differential array dx5(i) through dx40(i) is determined in each zone length D, e.g., in a range i=1 through 400 for the first zone (see FIG. 7). The determined maximum value is used as a peak array P(d) in each zone length D where d represents a parameter for identifying the zone and has a value in the range from 1 to (max/400).

In step S9, the peak array P(d) is separated into an area including a defect M and a normal area not including a defect M. Specifically, the zone length D may not necessarily contain a signal change due to a defect M, but a normal zone may possibly contain some coating irregularities of the photosensitive emulsion. Since small signal changes in each zone length D appear as a peak array P(d), they need to be separated. In FIG. 7, P(1), P(4), P(6) represent signals due to defects M, and P(2), P(3), P(5) represent signals due to coating irregularities in normal areas.

In order to separate coating irregularities due to defects M and coating irregularities in normal areas from each other, a maximum one of peak arrays P(d), P(d+1), P(d+2) in three adjacent zones (reference lengths) is selected as a maximum value array H(d) (extremal value calculator), and a minimum one of them is selected as a minimum value array L(d).

Specifically, the maximum value array H(d) with respect to the data signals shown in FIG. 7 is represented by P(1), P(4), P(4), P(6), . . . , and the minimum value array L(d) by P(2), P(2), P(5), P(5), . . . . The peak array P(d) may be selected in four or more zones.

In step S10, the maximum value array H(d) is approximated by two functions to determine a defect disappearing position Q where a defect M disappears. Specifically, the value of the maximum value array H(d) including a defect M can be considered as being progressively reduced, and the value of the maximum value array H(d) of a normal area not including a defect M can be considered as exhibiting no increasing or decreasing tendency. Therefore, the position of a zone where two functions established according to these characteristics change can be determined as the defect disappearing position Q.

Figure 8:
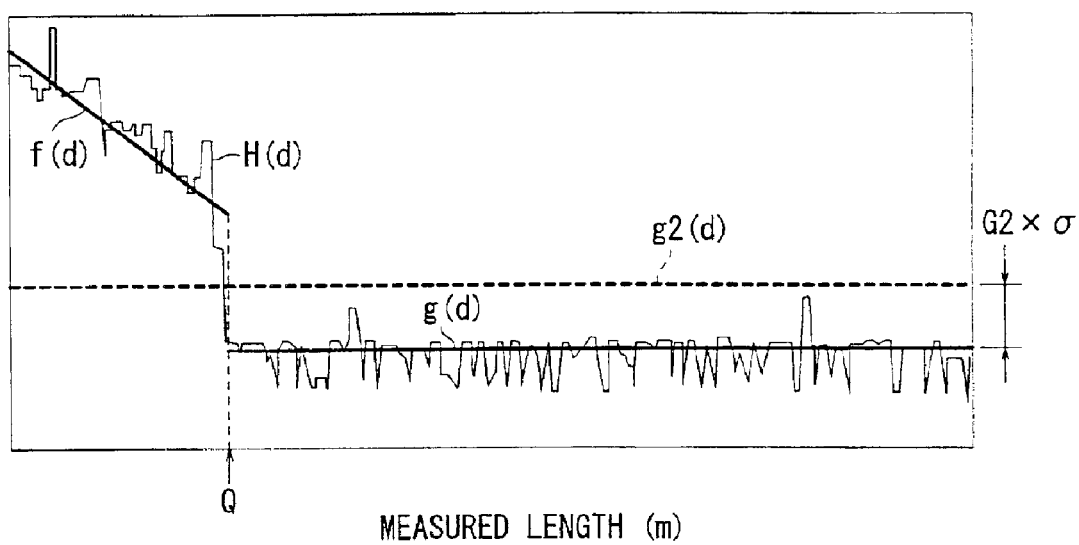
FIG. 8 is a graph showing two functions approximating a maximum value array and a defect disappearing position.

FIG. 8 shows the value of the maximum value array H(d) plotted in the direction in which the film 50 is measured. In FIG. 8, a function closer to the end (to the left in FIG. 8) of the film 50 than a defect disappearing position Q to be determined is established according to the following equation (2) (first function):

$$f(d)=\alpha d+\beta (d \leq Q) \quad (2)$$

A function subsequent to (to the right in FIG. 8) the defect disappearing position Q remoter from the end of the film 50 is established according to the following equation (3) (second function):

$$g(d)=\gamma (d>Q) \quad (3)$$

The function g(d) may not be constant.

The values $\alpha$, $\beta$, $\gamma$, and Q are determined to minimize an evaluation value S according to the following evaluation equation (4) for the two functions based on the method of least square errors:

$$S=\Sigma_{d=1 \to Q}(H(d)-f(d))^2 + G1 \times \Sigma_{d=(Q+1) \to max}(H(d)-g(d))^2 \quad (4)$$

where G1 represents a safety coefficient. The distance up to the defect disappearing position Q is adjusted to a longer distance by setting G1 to a larger value. In the equation (4), $\Sigma_{d=1 \to Q}(H(d)-f(d))^2$ represents a calculation for adding the square value in the parentheses while changing d from 1 to Q, and $\Sigma_{d=(Q+1) \to max}(H(d)-g(d))^2$ represents a calculation for adding the square value in the parentheses while changing d from (Q+1) to max.

The safety coefficient G1 may be set to about 3. In the equations (2), (3), (4), the parameter d representing the position of a zone may be replaced with the length x(m) of the film 50 which is related to d according to $x=d \times 400/1000$.

For example, the values $\alpha$, $\beta$, $\gamma$, and Q may be determined by determining $\alpha$, $\beta$ in the equation (2) according to the method of least square errors with the data near the end of the film 50 where a defect M is developed, determining $\gamma$ in the equation (3) with the data near the other end of the film 50, and putting the determined $\alpha$, $\beta$, $\gamma$ into the equation (4), and determining Q by changing the value of the defect disappearing position Q and finding it when S is minimum.

Alternatively, three of $\alpha$, $\beta$, $\gamma$, and Q in the equation (4) may be fixed to temporary values, and the remaining one is used as a parameter and changed to find a point where S is minimum. Thereafter, the remaining three may be processed in a similar manner, and the process is continuously performed to determine $\alpha$, $\beta$, $\gamma$, and Q to converge the value of S to a minimum value.

Figure 9:
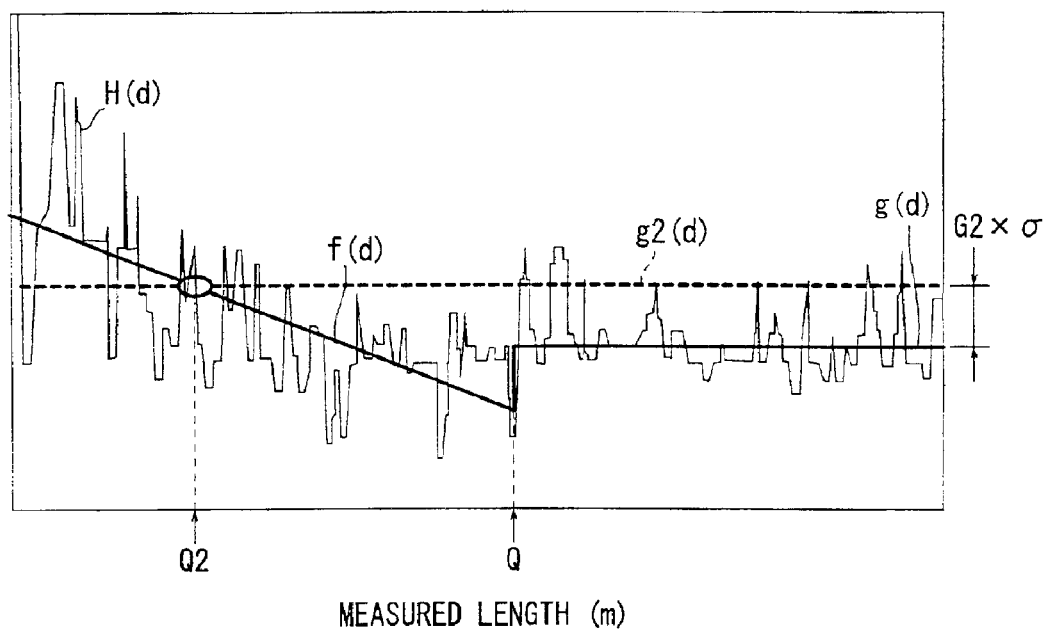
FIG. 9 is a graph showing two corrected functions approximating a maximum value array and a defect disappearing position.

If the defect disappearing position Q is determined as described above (defect disappearing position identifier), then if H(d) has a waveform shown in FIG. 9, the values of H(d) before and after the defect disappearing position Q do not differ from each other, and this position may not be suitable for use as a length of the film 50 to be discarded.

In step S11, the function g(d) according to the equation (3) is corrected using the following coefficient (G2×σ), producing a new function g2(d) (function corrector):

$$g2(d)=g(d)+G2 \times \sigma \quad (5)$$

where G2 represents a weighting coefficient in view of noise contained in the detected data signal, and σ represents a standard deviation of the minimum value array L(d). A point of intersection between the function g2(d) and the function f(d) can be determined as a corrected defect disappearing position Q2 (defect disappearing position corrector).

As shown in FIG. 8, if there is no point of intersection between the function g2(d) and the function f(d) in the range of d<Q, then the original defect disappearing position Q may be regarded as the corrected defect disappearing position Q2.

Since the minimum value array L(d) represents a signal produced by a coating irregularity of the photosensitive emulsion in a normal area, variations in the normal area of the components of the maximum value array H(d) may be canceled out by multiplying the standard deviation σ and the weighting coefficient G2 and adding the multiplied value to g(d).

After the corrected defect disappearing position Q2 is determined with respect to the data signals from the light-detecting unit A1, the processing in steps S7 through S11 is similarly effected on data signals from the light-detecting units A2 through A12, determining respective corrected defect disappearing positions Q2.

In step S12, a range of the film 50 to be discarded is determined from the corrected defect disappearing positions Q2 that have been determined with respect to the signal data in the channels of the light-detecting units A1 through A12.

Figure 10:
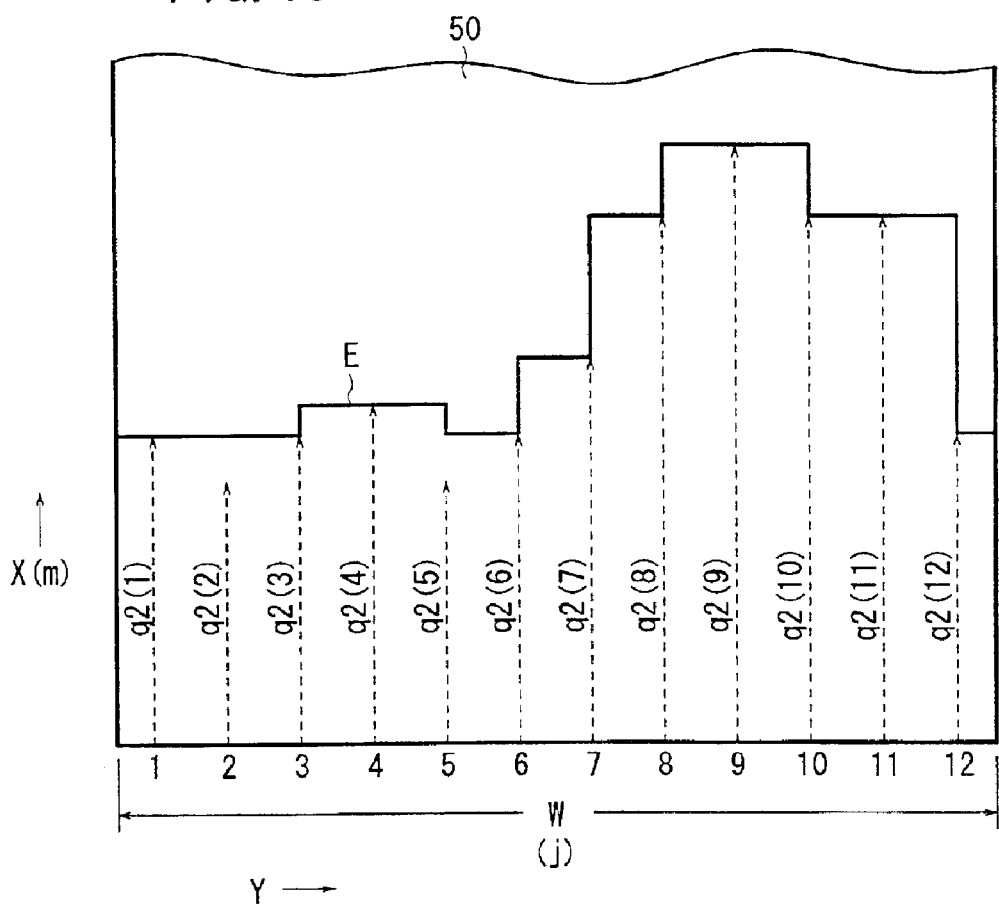
FIG. 10 is a diagram illustrative of a procedure for determining a sheet body length to be discarded at each of intervals between light-detecting units.

FIG. 10 shows a length E to be discarded from the end of the film 50 where the positions of the light-detecting units A1 through A12 are represented by j=1 through 12 and the corrected defect disappearing positions Q2 determined from the light-detecting units A1 through A12 are represented by q2(j). In the width from (j−1) to j, a larger one of q2(j−1) and q2(j) may be selected as the length E to be discarded. The values of q2(1) and q2(12) may be applied to the ends of the film 50 in the transverse direction, i.e., along the Y-axis.

In step S12, the length E to be discarded may be determined based on the defect disappearing positions Q rather than the corrected defect disappearing positions Q2.

By thus determining the length E to be discarded, only a minimum length required is determined to be discarded from the film 50.

In the above description, the sheet body is inspected while it is being wound around the core. However, the sheet body may be inspected while it is being fed, or may be inspected by moving the sensor system 14 relatively to the sheet body while the sheet body is being fixed.

With the apparatus for and the method of inspecting a sheet body according to the present invention, as described above, defects in the sheet body can be detected without manual intervention and without the need for sampling the sheet body. Therefore, defects in the sheet body can be detected accurately regardless of the individual different tendencies of workers.

If the sheet body comprises the film 50, then it is prevented from being exposed to visible light as an infrared radiation having a wavelength ranging from 940 nm to 1310 nm is used. Accordingly, images on the film 50 do not need to be developed in order to detect defects M therein.

For detecting data signals including defects M, the slits 22a, 32a inclined at the angle ψ equal to the angle of the defects M are disposed in front of the light-emitting units L1 through L12 and the light-detecting units A1 through A12. Therefore, when a defect M reaches the optical axis C, a change which is caused in the amount of light is very large, allowing a signal change to be detected reliably.

Furthermore, inasmuch as the optical axis C is inclined the angle θ to the normal to the film 50, the length of the path of light is increased and the transmittance is reduced, resulting in an increase in contrast which is effective to detect defects M highly reliably.

The condensing lens 36 is located such that the photoelectric transducer 34 has its photosensitive surface positioned at the focal point thereof. Therefore, even if the film 50 is positionally displaced along the axis C while it is being fed, the level of light detected by the photoelectric transducer 34 is not largely adversely affected by such a positional displacement of the film 50.

The 12 light-emitting units L1 through L12 and the 12 light-detecting units A1 through A12 are positioned at equal spaced intervals transversely along the width W of the film 50, and output signals from the light-emitting units L1 through L12 and the light-detecting units A1 through A12 are individually processed. Consequently, defects M are prevented from being detected in error due to coating irregularities of the photosensitive emulsion along the width W of the film 50 and sensitivity irregularities of the light-detecting units A1 through A12.

In the processing carried out by the processing device 12, data signals are divided according to the zone length D, three successive zones are used as a reference length, and a maximum value array H(d) is determined as a maximum value in that range. Consequently, a signal change due to a defect M can reliably be extracted.

Because the maximum value array H(d) is approximately processed by two functions, it is easy to identify the defect disappearing position Q.

Moreover, since one of the two functions f(d), g(d) is corrected with a coefficient, the maximum value array H(d) is applicable even if its waveform is of an irregular shape. The detected defect disappearing position Q can be adjusted to automatically set a desired length to be discarded for the film 50.

Another application of the apparatus for and the method of inspecting a sheet body according to the present invention will be described below.

The inventor has confirmed that the maximum value array H(d) obtained by the above apparatus for and the method of inspecting a sheet body is highly reproducible and exhibits an inherent waveform for each different film 50. Specifically, after the same film 50 has been inspected repeatedly a plurality of times, the obtained maximum value arrays H(d) have substantially the same values, and exhibits different waveforms for the respective films 50.

In general, a film 50 cannot be marked with a product number or the like because of its product characteristics. However, the maximum value array H(d) of a film 50 may be recorded thereon, and the product number of the film 50 can be identified from the recorded maximum value array H(d) by re-inspecting the film 50 as required.

A film 50 may suffer other defects than the defects M. These other defects are detected and recorded according to another inspecting process, and areas of the film which contain those defects are discarded in a subsequent process.

In the process of manufacturing the film 50, an end of the film 50 may occasionally be cut off by several meters. If an end of the film 50 is thus cut off, then the recorded positional information about defects is shifted, making it difficult to positionally identify those defects with accuracy. In order to discard the defective areas, it is customary to discard a length of 100±20 m from the end of the film 50 even if a small defect is present at a position that is 100 m spaced from the end of the film 50.

Using the maximum value array H(d), it is possible to identify a reference point on the film 50 in the longitudinal direction thereof, and hence the position of a defect on the film 50 can be calculated accurately based on the reference point.

For example, if the maximum value array H(d) exhibits an identifiable inherent value at a position that is 10 m spaced from the end of the film 50, then that position is established as a reference point, and a defect at a position that is 100 m spaced from the end of the film 50 can be identified as being spaced 90 m from the reference point.

Therefore, even if the end of the film 50 is cut off by 5 m, when the reference point is detected by re-inspecting the film 50, a length of 90±5 m may be discarded from the reference point. Consequently, a normal area of the film 50 is prevented from being discarded together with the defect.

Although a certain preferred embodiment of the present invention has been shown and described in detail, it should be understood that various changes and modifications may be made therein without departing from the scope of the appended claims.

What is claimed is:

1. An apparatus for inspecting a light-transmissive sheet body to detect a stripe defect therein, comprising:
    a light-emitting unit for applying light to the sheet body;
    a light-detecting unit for detecting light having passed through the sheet body;
    a slit member disposed in at least one of said light-emitting unit and said light-detecting unit, for shaping said light into a line of light through a slit defined in said slit member and guiding said line of light to said light-detecting unit; and
    a processor for processing signal data of the light detected by said light-detecting unit;
    said slit being oriented in the direction of the stripe defect, said processor comprising means for processing said signal data which is produced when said line of light is guided through said slit to said light-detecting unit to detect the stripe defect in said sheet body.
    wherein said processor comprises:
    an extremal value calculator for determining an extremal value of said signal data for each reference length of said sheet body; and
    a defect disappearing position identifier for determining a first function established by a plurality of extremal values obtained from a range including said defect in said sheet, and a second function established by a plurality of extremal values obtained from a range not including said defect in said sheet, and identifying a position on said sheet body where said first function changes to said second function, as a defect disappearing position where said defect disappears.

2. An apparatus according to claim 1, wherein said sheet body is fed relatively to said light-emitting unit and said light-detecting unit.

3. An apparatus according to claim 1, wherein said sheet body comprises a film coated with a photosensitive emulsion, and said stripe defect comprises a defect formed by a step provided by an end of the film as wound around a core before the photosensitive emulsion is applied to the film.

4. An apparatus according to claim 1, wherein said slit has a width in the range from 0.1 mm to 1.0 mm.

5. An apparatus according to claim 1, wherein said light emitted from said light-emitting unit and detected by said light-detecting unit travels along an optical axis inclined to the normal to said sheet body by an angle ranging from 5° to 70°.

6. An apparatus according to claim 1, wherein said light has a wavelength ranging from 940 nm to 1310 nm.

7. An apparatus according to claim 1, wherein said light-emitting unit and said light-detecting unit are provided in a plurality of pairs spaced along the width of said sheet body.

8. An apparatus according to claim 1, wherein said processor further comprises:
a function corrector for correcting said second function determined by said defect disappearing position identifier with a predetermined coefficient;
said defect disappearing position identifier comprising means for identifying a position on said sheet body where said first function changes to a corrected second function, as a corrected defect disappearing position where said defect disappears.

9. An apparatus according to claim 1, wherein said light-detecting unit comprises:
a condensing lens for converging the light having passed through said slit; and a photoelectric transducer disposed at the focal point of said condensing lens.

10. An apparatus for inspecting a light-transmissive sheet body to detect a stripe defect therein, comprising:
a light-emitting unit for applying light to the sheet body;
a light-detecting unit for detecting light having passed through the sheet body;
a slit member disposed in at least one of said light-emitting unit and said light-detecting unit, for shaping said light into a line of light through a slit defined in said slit member and guiding said line of light to said light-detecting unit;
a processor for processing signal data of the light detected by said light-detecting unit;
an extremal value calculator for determining an extremal value of said signal data for each reference length of said sheet body; and
a defect disappearing position identifier for determining a first function established by a plurality of extremal values obtained from a range including said defect in said sheet, and a second function established by a plurality of extremal values obtained from a range not including said defect in said sheet, and identifying a position on said sheet body where said first function changes to said second function, as a defect disappearing position where said defect disappears.

11. An apparatus according to claim 10 wherein said processor comprises:
a function corrector for correcting said second function determined by said defect disappearing position identifier with a predetermined coefficient;
said defect disappearing position identifier comprising means for identifying a position on said sheet body where said first function changes to a corrected second function, as a corrected defect disappearing position where said defect disappears.

12. An apparatus according to claim 10 wherein a range representing ½ through ⅓ of a minimum interval of defects is used as a zone length, said reference length being established as the sum of three successive zone lengths.

13. An apparatus according to claim 10, wherein said light-emitting unit and said light-detecting unit are provided in a plurality of pairs spaced along the width of said sheet body, and said defect disappearing position identifier comprises means for identifying said defect disappearing position for each of the pairs of said light-emitting unit and said light-detecting unit and regarding a greater length from an edge to said defect disappearing position of adjacent defect disappearing positions as a length to be discarded of said sheet body.

14. A method of inspecting a light-transmissive sheet body to detect a stripe defect therein, comprising the steps of:
detecting light emitted from a light-emitting unit having passed through the sheet body with a light-detecting unit as a line of light oriented in the direction of the stripe defect,
wherein said light-emitting unit and said light-detecting unit are provided in a plurality of pairs spaced at equal intervals along the width of said sheet body;
processing signal data obtained from said line of light with a processor to detect the stripe defect in said sheet body;
determining an extremal value of said signal data for each reference length of said sheet body; and
determining a first function established by a plurality of extremal values obtained from a range including said defect in said sheet, and a second function established by a plurality of extremal values obtained from a range not including said defect in said sheet, and identifying a position on said sheet body where said first function changes to said second function, as a defect disappearing position where said defect disappears.

15. An apparatus according to claim 7, wherein a pair in said plurality of pairs comprises a light-emitting unit and a light-detecting unit.

16. An apparatus according to claim 1, wherein only one slit is defined in said slit member.

17. An apparatus according to claim 7, wherein said light-emitting unit and said light-detecting unit provided in a plurality of pairs are spaced at equal intervals along the width of said sheet body.

18. An apparatus according to claim 9, wherein said light-detecting unit further comprises:
a light shielded housing which houses said condensing lens and said photoelectric transducer.

19. An apparatus according to claim 1, wherein the stripe defect is perpendicular to a conveyance-direction of the sheet.

* * * * *